United States Patent
Xue et al.

(10) Patent No.: US 11,610,123 B2
(45) Date of Patent: *Mar. 21, 2023

(54) CONTEXT AND DOMAIN SENSITIVE SPELLING CORRECTION IN A DATABASE

(71) Applicant: MYFITNESSPAL, INC., San Francisco, CA (US)

(72) Inventors: Wenzhe Xue, San Francisco, CA (US); Hesamoddin Salehian, San Francisco, CA (US); Patrick Howell, San Francisco, CA (US)

(73) Assignee: MyFitnessPal, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/379,065

(22) Filed: Jul. 19, 2021

(65) Prior Publication Data
US 2021/0342693 A1    Nov. 4, 2021

Related U.S. Application Data

(63) Continuation of application No. 15/680,351, filed on Aug. 18, 2017, now Pat. No. 11,087,210.

(51) Int. Cl.
*G06N 3/08* (2006.01)
*G06N 3/04* (2006.01)
(Continued)

(52) U.S. Cl.
CPC ............... *G06N 3/08* (2013.01); *G06F 16/35* (2019.01); *G06F 16/353* (2019.01);
(Continued)

(58) Field of Classification Search
CPC ...... G06F 40/126; G06F 40/274; G06F 40/40; G06F 40/44; G06F 40/45; G06F 40/47;
(Continued)

(56) References Cited

U.S. PATENT DOCUMENTS 7,251,665 B1    7/2007    Dunning et al.
8,176,419 B2    5/2012    Zhu et al.
(Continued)

FOREIGN PATENT DOCUMENTS

| JP | 2011008784 A | * | 1/2011 | ........... G06F 17/273 |
| WO | WO-2010013228 A1 | * | 2/2010 | ............. G06F 17/21 |
| WO | WO-2014151351 A1 | * | 9/2014 | ......... G06F 16/9535 |

OTHER PUBLICATIONS

Sutskever, Ilya et al., Sequence to Sequence Learning with Neural Networks, arXiv: 1409.3215v3 {cs.CL], Dec. 14, 2014.

*Primary Examiner* — Chau T Nguyen
(74) *Attorney, Agent, or Firm* — Maginot, Moore & Beck, LLP

(57) ABSTRACT

A method of operating a health tracking system is disclosed. The method comprises: receiving a first data record comprising at least a first descriptive string regarding a consumable item, the first descriptive string having at least one word thereof incorrectly spelled; generating a vector using the first descriptive string using a machine learning model; identifying a second descriptive string which corresponds to the consumable item and which has a correct spelling of the at least one incorrectly spelled word by applying the machine learning model to the generated vector; calculating a confidence factor regarding the identified second descriptive string using the machine learning model; and when it is determined that the confidence factor exceeds a predetermined threshold, (i) modifying the first data record by replacing the first descriptive string with the second descriptive string, and (ii) storing the modified first data record in the database.

14 Claims, 9 Drawing Sheets

(51) Int. Cl.
*G16H 20/60* (2018.01)
*G16H 40/67* (2018.01)
*G16H 20/30* (2018.01)
*G06F 40/35* (2020.01)
*G06F 40/56* (2020.01)
*G06F 16/35* (2019.01)
*G06N 20/00* (2019.01)
*G06F 40/232* (2020.01)
*G06F 40/284* (2020.01)

(52) U.S. Cl.
CPC .......... *G06F 16/355* (2019.01); *G06F 40/232* (2020.01); *G06F 40/284* (2020.01); *G06F 40/35* (2020.01); *G06F 40/56* (2020.01); *G06N 3/0445* (2013.01); *G06N 20/00* (2019.01); *G16H 20/30* (2018.01); *G16H 20/60* (2018.01); *G16H 40/67* (2018.01)

(58) Field of Classification Search
CPC .......... G06F 40/55; G06F 40/56; G06F 40/58; G06F 40/232; G06F 40/284; G06F 40/35; G06F 16/35; G06F 16/353; G06F 16/355; G16H 40/67; G16H 20/30; G16H 20/60; G06N 20/00; G06N 3/08; G06N 3/0445
See application file for complete search history.

(56) References Cited

U.S. PATENT DOCUMENTS

| | | | |
|---|---|---|---|
| 9,037,967 | B1 | 5/2015 | Al-Jefri et al. |
| 10,762,293 | B2* | 9/2020 | Ramerth ............... G06F 40/232 |
| 11,170,166 | B2* | 11/2021 | Bellegarda ............. G06N 20/00 |
| 2008/0147637 | A1 | 6/2008 | Li et al. |
| 2009/0164890 | A1 | 6/2009 | Zhu et al. |
| 2012/0303355 | A1* | 11/2012 | Liu ....................... G06F 40/126 704/9 |
| 2012/0323967 | A1* | 12/2012 | Ju ........................... G06F 16/93 707/E17.014 |
| 2013/0173258 | A1 | 7/2013 | Liu et al. |
| 2014/0195544 | A1* | 7/2014 | Whitman .............. G06F 16/435 707/744 |
| 2014/0200879 | A1 | 7/2014 | Sakhai et al. |
| 2016/0092557 | A1 | 3/2016 | Stojanovic et al. |
| 2016/0350655 | A1 | 12/2016 | Weiss |
| 2017/0193091 | A1 | 7/2017 | Byron et al. |
| 2017/0308790 | A1 | 10/2017 | Nogueira Dos Santos et al. |
| 2018/0157664 | A1 | 6/2018 | Howell et al. |
| 2019/0236471 | A1 | 8/2019 | Katz et al. |
| 2019/0295440 | A1 | 9/2019 | Hadad et al. |

\* cited by examiner

500

510

Store a plurality of data records, each of the plurality of data records comprising at least a descriptive string and nutritional data regarding a respective consumable item.

520

Filter the plurality of data records to identify a subset thereof, the subset comprising those records in which the respective descriptive strings have correct spellings of every word contained therein.

530

Generate, for each data record in the identified subset of the plurality of data records, a plurality of companion descriptive strings, each of the companion descriptive strings comprising an incorrect spelling of at least one word contained therein.

540

Train a machine learning model using pairs of descriptive strings, each pair of descriptive strings including (i) the descriptive string of a respective data record in the identified subset of the plurality of data records, and (ii) a corresponding one of the companion descriptive strings having at least one word thereof incorrectly spelled.

FIG. 5

CONTEXT AND DOMAIN SENSITIVE SPELLING CORRECTION IN A DATABASE

CROSS-REFERENCE TO RELATED APPLICATIONS

This application is a continuation of and claims the benefit of U.S. patent application Ser. No. 15/680,351, filed Aug. 18, 2017, the entire contents of which are incorporated herein by reference.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

FIELD

The methods and systems disclosed in this document relate health tracking systems having a food database and, more particularly, to context and domain sensitive spelling correction of entries in such a food database.

BACKGROUND

In recent years, health and fitness tracking applications that track food consumption have become very popular. Food consumption is important to a healthy lifestyle and a person's diet is well known to be related to various health conditions, such as diabetes and obesity to name a few. Health and fitness tracking applications allow users to set and achieve personalized health goals by tracking the foods and beverages that they consume. These applications enable users to gain insights that help them make smarter choices and create healthier habits. Accordingly, it would be advantageous to provide users with health tracking systems that enable entry of the foods and beverages for tracking with minimized errors.

SUMMARY

In accordance with one exemplary embodiment of the disclosures, a method of operating a health tracking system is disclosed. The method comprises receiving a first data record comprising at least a first descriptive string and nutritional data regarding a consumable item, the first descriptive string having at least one word thereof incorrectly spelled; generating a vector with the first descriptive string of the first data record using a machine learning model; identifying a second descriptive string which corresponds to the consumable item and which has a correct spelling of the at least one incorrectly spelled word by applying the machine learning model to the generated vector; calculating a confidence factor regarding the identified second descriptive string using the machine learning model; and when it is determined that the confidence factor exceeds a predetermined threshold: modifying the first data record by replacing the first descriptive string with the second descriptive string; and storing the modified first data record in a database.

Pursuant to another exemplary embodiment of the disclosures, a health tracking system is disclosed. The health tracking system comprises a database configured to store a plurality of data records, each of the plurality of data records comprising at least a descriptive string and nutritional data regarding a respective consumable item; and a data processor in communication with the database. The data processor is configured to: filter the plurality of data records to identify a subset thereof, the subset comprising those records in which the respective descriptive strings have correct spellings of every word contained therein; generate, for each data record in the identified subset of the plurality of data records, a plurality of companion descriptive strings, each of the companion descriptive strings comprising an incorrect spelling of at least one word contained therein; train a machine learning model using pairs of descriptive strings, each pair of descriptive strings including (i) the descriptive string of a respective data record in the identified subset of the plurality of data records, and (ii) a corresponding one of the companion descriptive strings having at least one word thereof incorrectly spelled; receive a first descriptive string having at least one word thereof incorrectly spelled; and use the trained machine learning model to output a second descriptive string to replace the first descriptive string, the second descriptive string having a correct spelling of the at least one incorrectly spelled word.

In accordance with yet another exemplary embodiment, a further method of operating a health tracking system having a database configured to store a plurality of data records, each of the plurality of data records comprising at least a descriptive string and nutritional data regarding a respective consumable item is disclosed. The method comprises: receiving a first descriptive string having at least one word thereof incorrectly spelled; generating a vector with the first descriptive string using a machine learning model; identifying a second descriptive string which has a correct spelling of the at least one incorrectly spelled word by applying the machine learning model to the generated vector; calculating a confidence factor regarding the second descriptive string using the machine learning model; when it is determined that the confidence factor exceeds a predetermined threshold, searching the database to identify a first subset of data records in the plurality of data records having descriptive strings that are similar to the second descriptive string; and when it is determined that the confidence factor is below the predetermined threshold, searching the database to identify a second subset of data records in the plurality of data records having descriptive strings that are similar to the first descriptive string.

These and other aspects of the disclosure shall become apparent when considered in light of the disclosure provided herein.

BRIEF DESCRIPTION OF THE DRAWINGS

The foregoing aspects and other features of a health and fitness tracking system are explained in the following description, taken in connection with the accompanying drawings.

FIG. 5 shows a method of operating the health tracking system to train the spelling correction model using consumable records in the database.

Figure 1:
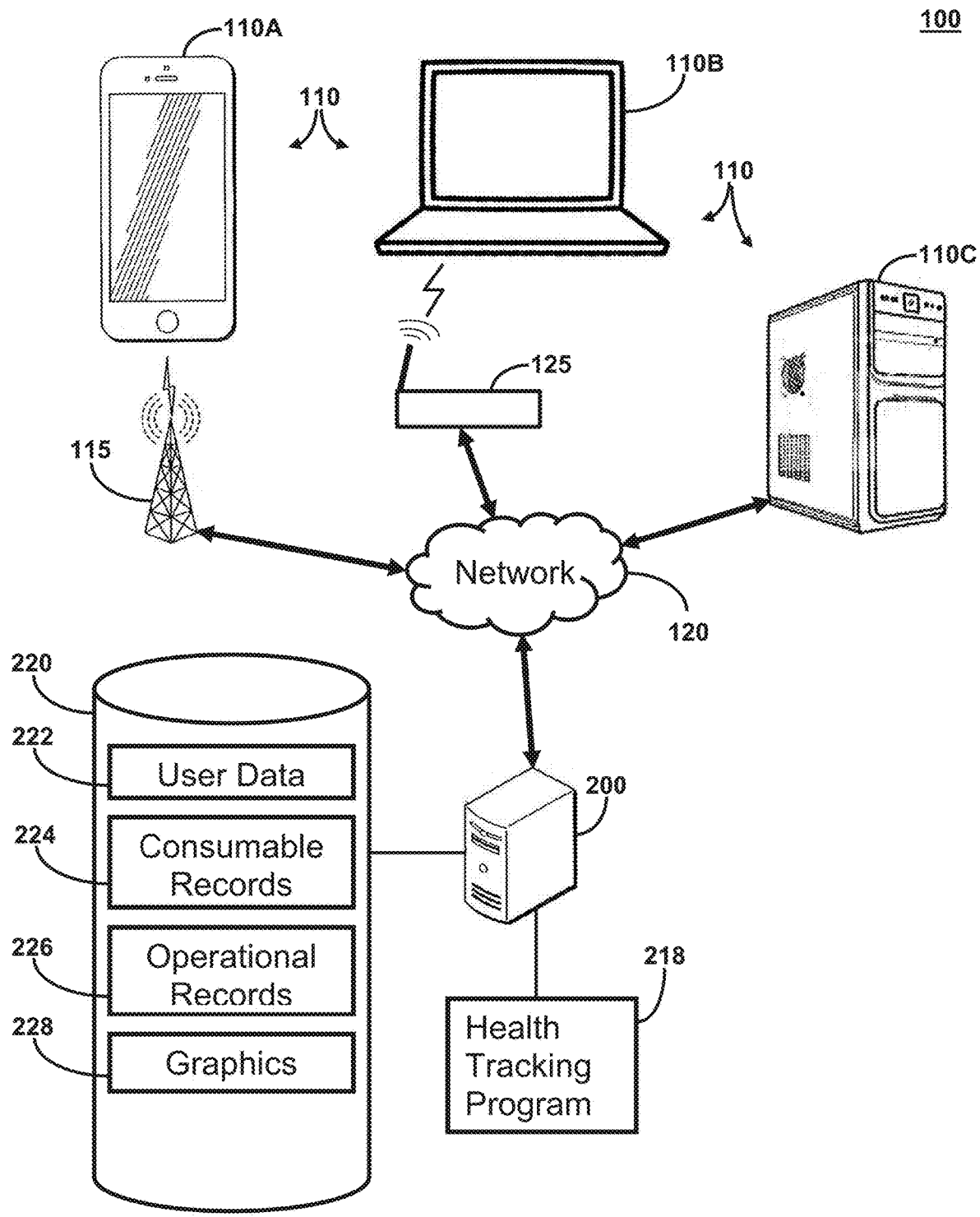
FIG. 1 shows a health tracking system.

All Figures ©MyFitnessPal, Inc. 2021. All rights reserved.

DETAILED DESCRIPTION

In the following detailed description, reference is made to the accompanying figures which form a part hereof wherein like numerals designate like parts throughout, and in which is shown, by way of illustration, embodiments that may be practiced. It is to be understood that other embodiments may be utilized, and structural or logical changes may be made without departing from the scope of the present disclosure. Therefore, the following detailed description is not to be taken in a limiting sense, and the scope of embodiments is defined by the appended claims and their equivalents.

Aspects of the disclosure are disclosed in the accompanying description. Alternate embodiments of the present disclosure and their equivalents may be devised without parting from the spirit or scope of the present disclosure. It should be noted that any discussion herein regarding "one embodiment", "an embodiment", "an exemplary embodiment", and the like indicate that the embodiment described may include a particular feature, structure, or characteristic, and that such particular feature, structure, or characteristic may not necessarily be included in every embodiment. In addition, references to the foregoing do not necessarily comprise a reference to the same embodiment. Finally, irrespective of whether it is explicitly described, one of ordinary skill in the art would readily appreciate that each of the particular features, structures, or characteristics of the given embodiments may be utilized in connection or combination with those of any other embodiment discussed herein.

Various operations may be described as multiple discrete actions or operations in turn, in a manner that is most helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B and C).

The terms "comprising," "including," "having," and the like, as used with respect to embodiments of the present disclosure, are synonymous.

As used herein, the term "consumable" refers to foods, beverages, dietary supplements, vitamin supplements, medication, and other items for consumption. As used herein, the term "consumable record" refers to a database record that relates to a particular consumable. Each consumable record comprises a plurality of data fields that relate to a particular consumable item. In some embodiments, each consumable record includes a description field that includes data, such as a text string, that identifies or describes the particular consumable. In some embodiments, each consumable record includes an ingredients field that includes data, such as one or more text strings, that list ingredients for a particular consumable. In some embodiments, each consumable record includes fields for caloric content, macronutrients, micronutrients, serving size, and other nutrition and health information.

Some health and fitness tracking applications use crowd-sourced food data to enable the tracking of foods and beverages that users consume. As a result, the food data often includes incorrect spelling and other typographical errors. These spelling and typographical errors are difficult to correct using traditional spelling correction methods because traditional spelling correction solutions make incorrect substitution. For example, given the incorrect phrase "low yat yogurt," a traditional spellchecker might correctly identify that the word "yat" is a misspelling, but improperly correct the phrase to instead recite "low cat yogurt." Even more problematic, given the incorrect phrase "finely hopped vegetables," a traditional spellchecker might entirely miss the misspelled word "hopped." In view of the foregoing, the herein-described systems and methods provide a health tracking system with context-sensitive and domain-sensitive spelling correction model in order to improve the quality of food data utilized by the health tracking system.

Health Tracking System

With reference to FIG. 1, an exemplary embodiment of a health tracking system 100 including context and domain sensitive spelling correction is shown. In the illustrated embodiment, the health tracking system 100 includes a plurality of health tracking devices 110 in communication with a system server 200 or other data processing system over a network 120 such as, e.g. the Internet.

The server 200 comprises a computerized device or data processing system configured to run one or more software applications on a processor thereof (e.g. the network-side health tracking program 218). The server 200 of the present embodiment is further configured to receive a plurality of consumable records which include item descriptions, as well as caloric and nutritional contents of a respective plurality of consumable items which are entered at the health tracking devices 110, other consumer devices, and/or provided from one or more manufacturing or distributing entities. The consumable records are stored at a storage apparatus or memory of the server 200 (e.g., consumable records 224).

The storage apparatus or memory is configured to store instructions including a network-side health tracking program 218 (which may also be referred to herein as the "health tracking application"), as well as a database 220 accessible by at least the health tracking program 218. The database 220 includes user data 222, consumable records 224, operational records 226, and graphics 228. Alternatively, the server 200 may be in communication with a separate storage entity (not shown) for storage thereof.

As will be discussed in further detail elsewhere herein, the server 200 utilizes a machine learning model to provide context and domain sensitive spelling correction. In one embodiment, the spelling correction is used to identify and correct spelling errors in newly created or existing consumable records 224. In one embodiment, the spelling correction is used to provide improved search results when a user searches the consumable records 224.

The health tracking devices 110 (which may also be referred to herein as "health and fitness tracking devices")

comprise any number of computerized apparatus, which include a user interface, such as e.g., a smartphone 110A, laptop computer 110B, a tablet computer, a smart watch, a desktop computer 110C, or other such device. In at least one embodiment, the user interface may comprise an LCD touch screen or the like, a mouse or other pointing device, a keyboard or other keypad, speakers, and a microphone, as will be recognized by those of ordinary skill in the art. The user interface provides the user with any of various health, fitness and activity related data such as food and nutritional consumption, calorie expenditure, sleep metrics, weight, body fat, heart rate, distance travelled, steps taken, etc. In order to connect to the network 120, the health tracking devices 110 are generally configured to utilize any of various wired or wireless communications components, infrastructures and systems, such as cell towers 115 of a mobile telephony network, wireless routers 125, Bluetooth®, near field communication (NFC), or physical cables. Health tracking devices 110 may use data collected from sensors associated to or in communication with the health tracking device 110, such as heart rate monitors, step counters, stair counters, global positioning system ("GPS") tracking devices, as well as various other motion tracking and biometric monitoring devices; alternatively, or in addition, a user may manually enter health related data. Such sensors allow the user to easily track and automatically log activity and/or consumption information with the health tracking device. In addition, the health tracking device 110 may include one or more cameras configured to obtain health parameter data including e.g., capture images of a user's performance of an activity and/or capture images of consumed items or descriptions thereof (including barcodes or other machine readable identifiers).

The health tracking devices 110 are configured to communicate with the system server 200 in order to enable: accessing and searching of the consumable records 224 stored thereat, display of the consumable records, provide additional records, and/or enable the user to select individual ones of the displayed consumable records for the purposes of caloric and nutritional logging. In one embodiment, foregoing functions are performed via execution of one or more software applications at the server 200 (i.e., server or network-side applications) in communication with one or more complementary software applications at the health tracking devices 110 (i.e., client-side applications). For example, the health tracking program 218, running on the processor (of the server 200) may be utilized to accomplish the foregoing, as explained in further detail below. A client-side software application for performing various functions necessary for the herein disclosed concepts may also be utilized (see health tracking application 316 of FIG. 3, discussed below).

System Server

Figure 2:
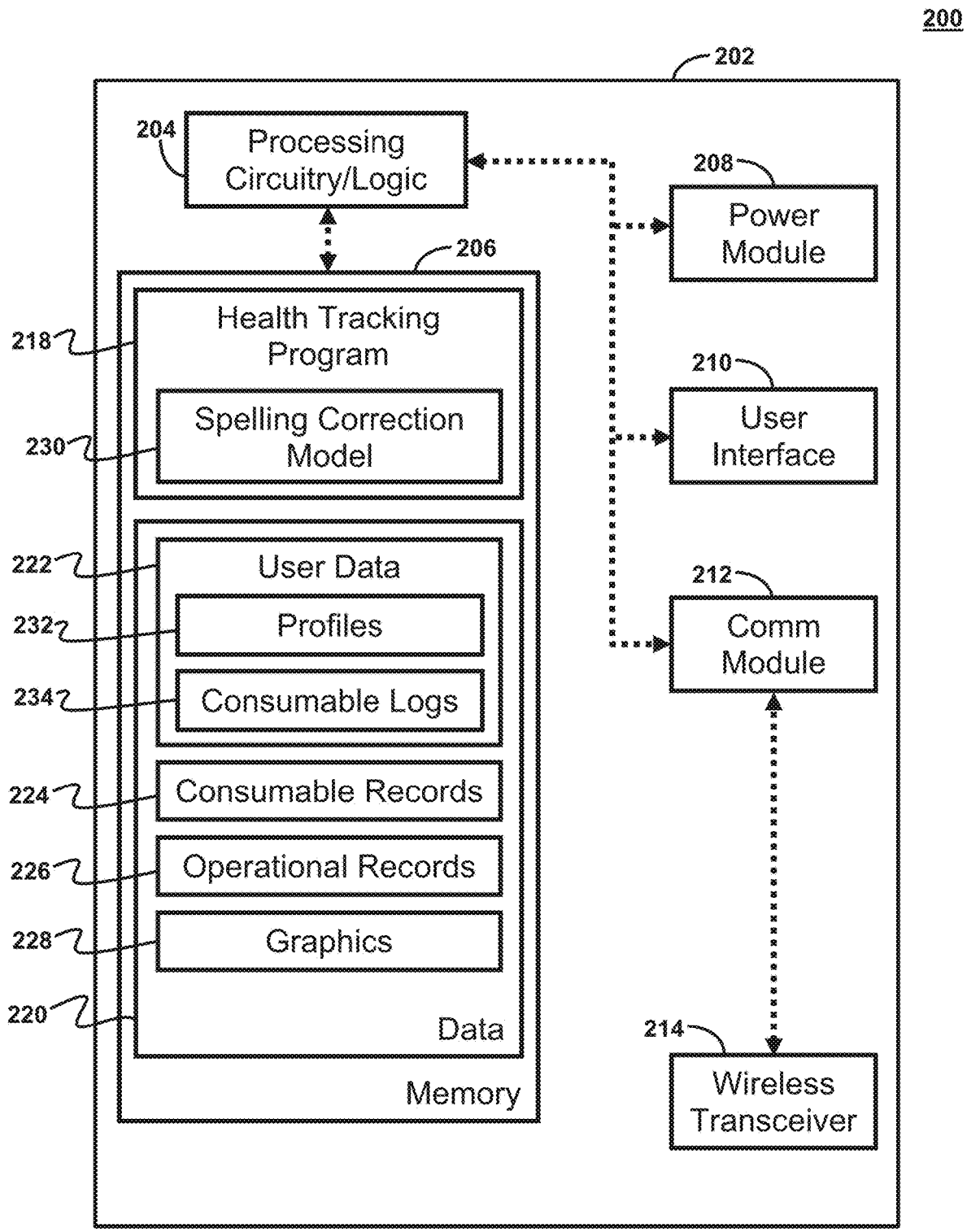
FIG. 2 shows a system server or data processing system of the health tracking system of FIG. 1.

With reference now to FIG. 2, a block diagram of an exemplary embodiment of the system server 200 of FIG. 1 is shown. It is appreciated that the embodiment of the system server 200 shown in FIG. 2 is only one exemplary embodiment of a system server 200. As such, the exemplary embodiment of the system server 200 of FIG. 2 is merely representative of any of various manners or configurations of system servers or other data processing systems that are operative in the manner set forth herein.

The system server 200 of FIG. 2 is typically provided in a housing, cabinet or the like 202 that is configured in a typical manner for a server or related computing device. In one embodiment, the system server 200 includes processing circuitry/logic 204, memory 206, a power module 208, a user interface 210, a network communications module 212, and a wireless transceiver 214.

The processing circuitry/logic 204 is operative, configured and/or adapted to operate the system server 200 including the features, functionality, characteristics and/or the like as described herein. To this end, the processing circuitry/logic 204 is operably connected to the memory 206, the power module 208, the user interface 210, the network communications module 212, and the wireless transceiver 214. The memory 206 may be of any type of device capable of storing information accessible by the processor, such as a memory card, ROM, RAM, write-capable memories, read-only memories, hard drives, discs, flash memory, or any of various other computer-readable medium serving as data storage devices as will be recognized by those of ordinary skill in the art. The memory 206 is configured to store instructions including a network-side health tracking application 218 for execution by the processing circuitry/logic 204, as well as a database 220 for use by at least the health tracking program 218. The database 220 includes user data 222, consumable records 224, operational records 226, and graphics 228. As discussed in greater detail below, the health tracking application 218 includes a spelling correction model 230 configured to provide context and domain sensitive spelling correction for the health tracking application 218.

With continued reference to FIG. 2, the power module 208 of the system server 200 is operative, adapted and/or configured to supply appropriate electricity to the system server 200 (i.e., including the various components of the system server 200). The power module 208 may operate on standard 120 volt AC electricity, but may alternatively operate on other AC voltages or include DC power supplied by a battery or batteries.

The network communication module 212 of the system server 200 provides an interface that allows for communication with any of various devices using various means. In particular, the network communications module 212 includes a local area network port that allows for communication with any of various local computers housed in the same or nearby facility. In some embodiments, the network communications module 212 further includes a wide area network port that allows for communications with remote computers over the Internet (e.g., network 120 of FIG. 1). Alternatively, the system server 200 communicates with the network 120 via a modem and/or router of the local area network. In one embodiment, the network communications module is equipped with a Wi-Fi transceiver 214 or other wireless communications device. Accordingly, it will be appreciated that communications with the system server 200 may occur via wired communications or via the wireless communications. Communications may be accomplished using any of various known communications protocols. In the embodiment of FIG. 2, the wireless transceiver 214 may be a Wi-Fi transceiver, but it will be recognized that the wireless transceiver may alternatively use a different communications protocol.

The system server 200 may be accessed locally by an authorized user (i.e., an administrator or operator). To facilitate local access, the system server 200 includes an interactive user interface 210. Via the user interface 210, an operator may access the instructions, including the health tracking application 218, and may collect data from and store data to the memory 206. In at least one embodiment, the user interface 210 may suitably include an LCD touch screen or the like, a mouse or other pointing device, a keyboard or other keypad, speakers, and a microphone, as will be recognized by those of ordinary skill in the art. Accordingly, the user interface 210 is configured to provide an administrator or other authorized user with access to the memory 206 and allow the authorized user to amend, manipulate and display information contained within the memory.

As mentioned above, the memory 206 includes various programs and other instructions that may be executed by the processor circuitry/logic 204. In particular, the memory 206 of the system server 200 of FIG. 2 includes the health tracking program 218 (which may also be referred to herein as a "health tracking application"). The health tracking program 218 is configured to cause the system server 200 to enable a user to obtain nutritional data related to any of various consumables. Execution of the health tracking application 218 by the processor circuitry/logic 204 results in signals being sent to and received from the user interface 210 and the communications module 212 (for further delivery to a user device such as a health tracking device 110), in order to allow the user receive and update various aspects of the consumable records 224. The network-side health tracking application 218 is configured to provide various graphical views and screen arrangements to be displayed to a user on a health tracking device 110.

The user data 222 includes at least user profiles 232 and corresponding consumable logs 234. The user profiles 232 include a profile data for each user of the health tracking system 100. Each user profile includes demographic information for the users such as name, age, gender, height, weight, performance level (e.g., beginner, intermediate, professional, etc.) and/or other information for the user. In at least one embodiment, the consumable logs 234 include a consumable diary/log for each user (which may also be referred to herein as a "food diary"). The consumable diary/log allows the user to track consumables that are consumed by the user over a period of days and any nutritional data associated with the food consumed. For example, the consumable diary/log may allow the user to enter particular consumable that is consumed by the user and keep track of the associated calories, macronutrients, micronutrients, sugar, fiber, and/or any of various other nutritional data associated with the consumables entered by the user in the consumable diary/log. In some embodiments, the user data 222 further includes various activity and fitness data collected by sensors (not shown) associated with the health tracking devices 110.

In an alternative embodiment, the foregoing profile data may be stored at a storage entity separate from yet in communication with the server 200. For example, a centralized server may be provided which is configured to store all data relating to an individual user in one storage area (including workout data, nutrition/consumption data, profile data, etc.).

A plurality of consumable records 224 is stored in the database 220. As discussed above, the term "consumable record" refers to a database record that relates to a particular consumable item. In at least one embodiment, each consumable record comprises a plurality of data fields that related to a particular consumable item. At least some consumable records 224 and/or fields are editable by users or may be created by users within the database 220 without the need for special authorization or privileges. In the disclosed embodiment, each of the consumable records includes a number of fields including, for example, a name for the consumable item, summary information about the consumable item, and detailed nutritional information about the consumable item. Detailed nutritional information about a consumable item may include one or more of: serving size, calories, nutrients, ingredients, or any other nutritional information about the item. For example, the detailed nutritional information may include information that may be provided on USDA food labels or state-regulated food labels (e.g., vitamin and mineral content, fat content, cholesterol content, protein content, sugar content, carbohydrate content, fiber content, organic contents, etc.). The summary information about the consumable may include some subset of the more detailed information about the consumable. For example, the summary information about the consumable may only include serving size and calorie information. The various fields of each consumable record may be populated by data from any user or third party data providers. Therefore, it will be recognized that in at least some embodiments, consumable records 224 may have been entered by any of various sources including an administrator or operator of the health tracking system 100, commercial food providers (e.g., food distributors, restaurant owners, etc.), and/or users of the health tracking system 100. In addition, certain information may be stored in a machine readable code (such as a bar code or QR code) which is captured via a camera or other scanner at the user device 110.

The operational records 226 include current and historical data stored by the system server 200 in association with operation of the system server 200, execution of the health tracking application 218, and/or manipulation of data 220 within the memory 206. For example, the operational records 226 may include information concerning amendments made to any of various consumable records 224. The operational records 226 may also include other information related to the control and operation of the system server 200, including statistical, logging, licensing, and historical information.

In one embodiment, graphical views 228 are provided at the server 200 which are pushed to the health tracking device 110 for display thereat of various screen arrangements.

While the system server 200 has been explained in the foregoing embodiment as housing the health tracking program 218 and the various records and databases in the memory 206, it will be recognized that in other embodiments these components may be retained in other one or more remote locations in communication with the health tracking system 100. For example, in at least one embodiment, the consumable records 224 may comprise data retained by a database separate from the system server 200. Alternatively, the consumable records 224 or certain fields of the consumable records 224 are received from a third party database. In such embodiments, the health tracking application may utilize any number of application programming interfaces (APIs) to access the data in the third party databases and incorporate such information for use in the health tracking application 218, without local storage thereof. Accordingly, it will be recognized that the description of the system server 200 of FIG. 2 is but one exemplary embodiment of a data processing system that may be utilized by the health tracking system 100.

A computer program product implementing an embodiment disclosed herein may therefore comprise one or more computer-readable storage media storing computer instructions executable by a processor to provide an embodiment of a system or perform an embodiment of a method disclosed herein. Computer instructions (e.g., the health tracking application 218 including the spelling correction model 230) may be provided by lines of code in any of various languages as will be recognized by those of ordinary skill in the art. A "non-transitory computer-readable medium" may be any type of data storage medium that may store computer instructions, including, but not limited to a memory card, ROM, RAM, write-capable memories, read-only memories, hard drives, discs, flash memory, or any of various other computer-readable medium.

Health Tracking Devices

With reference again to FIG. 1, the health tracking devices 110 may be provided in any of various forms. Examples of a health tracking devices 110 configured for use with the health tracking system 100 include a smartphone 110A, a laptop computer 110B, and a desktop computer 110C, as shown in FIG. 1, as well as various other electronic devices. Accordingly, it will be recognized that the health tracking devices 110 may comprise portable electronic devices such as the smartphone 110A or the laptop computer 110B, or stationary electronic devices such as the desktop computer 110C. Other examples of health tracking devices include, handheld or tablet computers, smart watches, portable media players, other wearable devices, or any of various other health tracking devices configured to receive entry of consumables (not shown).

In one embodiment, data entered at one device 110 may be provided to other ones of the user's devices 110. For example, data entered at the smart phone 110A may be provided to the desktop computer 110C and/or the laptop computer 110B for storage thereat. Alternatively or in addition, the data may be stored at a single network storage apparatus (not shown) having a dedicated portion of storage for records relating to the user and accessible by all of the user's devices 110.

Figure 3:
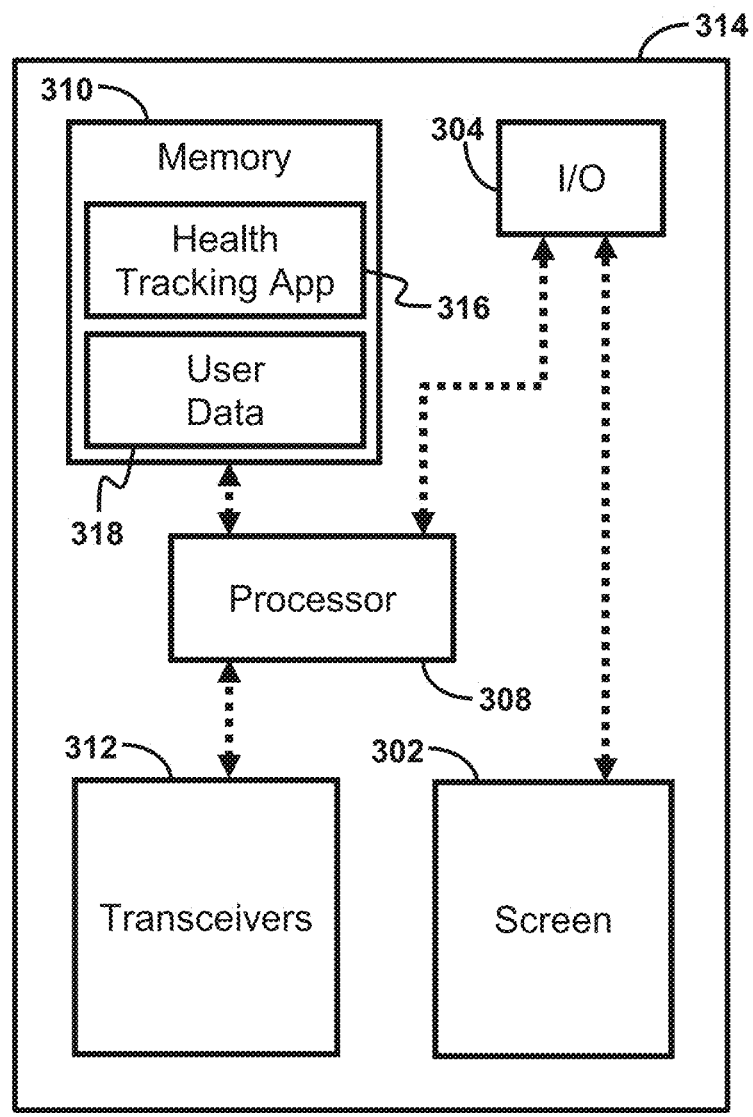
FIG. 3 shows a smart phone of the health tracking system of FIG. 1

With reference now to FIG. 3, in at least one embodiment the health tracking device 110 is provided in the form of a smartphone 110A. The smartphone 110A includes a display screen 302, an input/output (I/O) interface 304, a processor 308, a memory 310, and one or more transceivers 312. The smartphone 110A also includes a protective outer shell or housing 414 designed to retain and protect the electronic components positioned within the housing 414. The smartphone 110A also includes a battery (not shown) configured to power the display screen 302, processor 308, transceivers 312 and various other the electronic components within the smartphone 110A.

The display screen 302 of the smartphone 110A may be an LED screen or any of various other screens appropriate for the personal electronic device. The I/O interface 304 of the smartphone 110A includes software and hardware configured to facilitate communications with the user. The I/O interface 304 is in communication with the display screen 302 and is configured to visually display graphics, text, and other data to the user via the display screen 302. As will be recognized by those of ordinary skill in the art, the components of the health tracking device 110 may vary depending on the type of display device used. Alternative health tracking devices, such as the laptop 110B and the desktop 110C, may include much of the same functionality and components as the smartphone 110A shown in FIG. 3, but may not include all the same functionality or components and/or may include others not listed.

The processor 308 of the smartphone 110A may be any of various processors as will be recognized by those of ordinary skill in the art. The processor 308 is in communication with the I/O interface 304, the memory 310, and the transceivers 312, and is configured to deliver data to and receive data from each of these components. The memory 310 is configured to store information, including data and instructions for execution by the processor 308. It will be recognized by those of ordinary skill in the art that a "processor" includes any hardware system, hardware mechanism or hardware component that processes data, signals or other information. A processor may include a system with a central processing unit, multiple processing units, dedicated circuitry for achieving functionality, or other systems.

The transceivers 312 may be any of various devices configured for communication with other electronic devices, including the ability to send communication signals and receive communication signals. The transceivers 312 may include different types of transceivers configured to communicate with different networks and systems. Such transceivers are well known and will be recognized by those of ordinary skill in the art.

In some embodiments, the transceivers 312 include at least one transceiver configured to allow the smartphone 110A to perform wireless communications with the cell towers 115 of the wireless telephony network, as will be recognized by those of ordinary skill in the art. The wireless telephony network may comprise any of several known or future network types. For example, the wireless telephony network may comprise commonly used cellular phone networks using CDMA, GSM or FDMA communication schemes, as well as various other current or future wireless telecommunications arrangements. In some embodiments, the transceivers 312 include at least one transceiver configured to allow the smartphone 110A to communicate with any of various local area networks using Wi-Fi, Bluetooth® or any of various other communications schemes.

In some embodiments, the memory 310 includes program instructions for a graphical user interface configured to provide a client-side health tracking application 316. The memory 310 may further be configured to store certain user data 318, such as e.g., user gender, height, weight, user identifier, password, etc. Additionally, health related data (e.g., data collected from one or more sensors and/or manually entered) may be stored. The processor 308 is configured to read the program instructions from the memory 310 and execute the program instructions to provide the health tracking application 316 to the user so for the purpose of performing health and fitness related tasks for the user, including displaying, modifying, and analyzing the user data 318.

In at least one embodiment, the user data 318 includes a plurality of consumable records which serves as a log of consumables that have been consumed by the user for the purpose of caloric and nutritional tracking. That is to say, the client-side health tracking application 316 is configured to display consumable records and enable the user to select consumable records (from a plurality of records accessed via the network 120), those items that correspond to consumables that he or she has consumed are stored at the client-side for the purpose of logging the consumables in this embodiment. In another alternative, such log may be stored remote from the device and/or only kept at the device for a transitory period.

The memory 310 that retains the data and instructions may be of any type of device capable of storing information accessible by the processor, such as a memory card, ROM, RAM, write-capable memories, read-only memories, hard drives, discs, flash memory, or any of various other computer-readable medium serving as data storage devices as will be recognized by those of ordinary skill in the art. Portions of the system and methods described herein may be implemented in suitable software code that may reside within the memory as software or firmware. Alternatively, or in addition, the software (such as e.g., the client side health tracking program 316) may be downloaded from a network location, such as via the Internet.

Context and Domain Sensitive Spelling Correction Model

As discussed above, the health tracking application 218 is provided with a spelling correction model 230 configured to provide context and domain sensitive spelling correction for the health tracking application 218. The spelling correction model 230 comprises a machine learning model which has been trained using text fields of at least some of consumable records 224. As used herein, the term "machine learning model" refers to a system or set of program instructions configured to implement an algorithm or mathematical model that predicts and provides a desired output based on a given input. A machine learning model is not explicitly programmed or designed to follow particular rules in order to provide the desired output for a given input. Instead, the machine learning model is provided with a corpus of training data from which identifies or "learns" patterns and statistical relationships or structures in the data, which are generalized to make predictions with respect to new data inputs. In the case of supervised machine learning, training data is labeled as inputs and outputs and the machine learning model is trained to predict outputs for new data based on the patterns and other relationships or structures identified in the training data. However, the training data needn't necessarily be labeled as inputs and outputs, as is the case with unsupervised machine learning.

Figure 4:
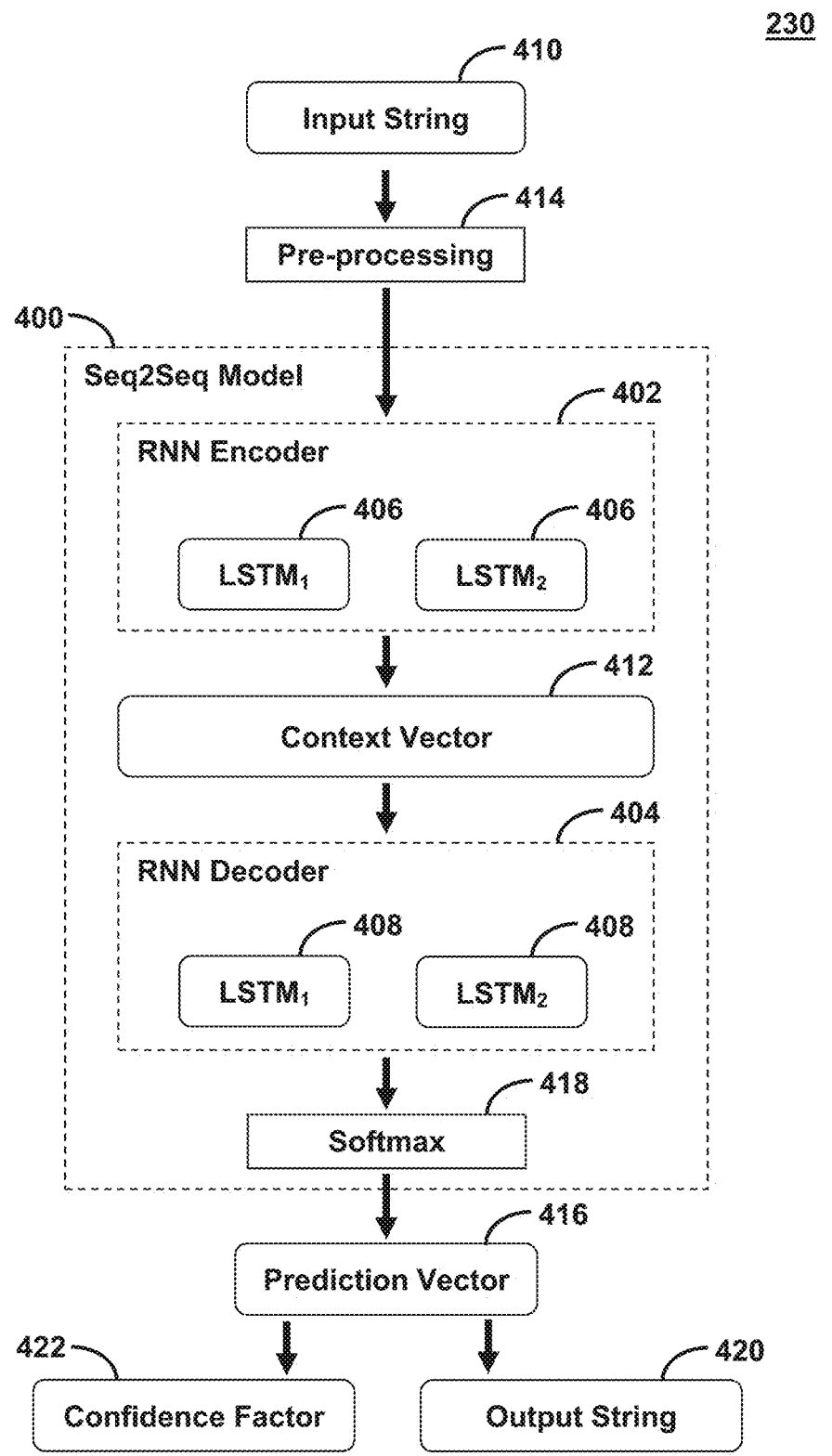
FIG. 4 shows a block diagram illustrating an exemplary embodiment of a spelling correction model.

FIG. 4 illustrates an exemplary embodiment of the spelling correction model 230. Particularly, the spelling correction model 230 is a system or set of program instructions configured to implement a sequence to sequence (Seq2Seq) model 400. The sequence to sequence model 400 is a type of deep learning model comprising two recurrent neural networks (RNN), an encoder 402 and a decoder 404. The encoder 402 comprises a plurality of Long Short Term Memory (LSTM) encoder layers 406. Similarly, the decoder 404 comprises a plurality of LSTM decoder layers 408. As illustrated, the model includes two LSTM encoder layers 406 and two LSTM decoder layers 408, but may include a different number LSTM encoder/decoder layers. In one embodiment, dropout layers (not shown) are included between each LSTM layer to prevent overfitting to training data. The dropout layers are configured to randomly mask network units during training of the model 400, which reduces overfitting to the training data. This helps to improve the generalization ability of the trained model in making predictions on new data not seen during the training process. In other words, overfitting on the training data means that the model learns to perform well on the training data but fails to generalize when making predictions on new data.

The encoder 402 is configured to receive a sequence of characters, e.g. an input text string 410, and to encode a context vector 412 based on the received sequence of characters. In some embodiments, the input text string 410 is preprocessed 414 before being provided to the encoder 402. Particularly, an end-of-sequence (EOS) character or token is appended to the input text string, which tells the LSTM encoder layers 406 when to terminate. Additionally, the input text string is padded with padding (PAD) tokens such that the input text string has a predetermined fixed length. In some embodiments, the sequence of characters comprising the input string 410 may be reversed to improve performance. As an example, an input string "Salt" might be transformed into "<PAD><PAD> . . . <PAD><EOS> t l a S" during the preprocessing step 414, prior to being provided to the encoder 402. Additionally, the encoder 402 always has a finite character vocabulary. Accordingly, characters in the input text string which are not in character vocabulary of the encoder 402 may be replaced with an unknown (UNK) character during preprocessing (e.g., the character "$" may be outside the character vocabulary of the model).

When the encoder 402 receives the processed string, the encoder 402 encodes the sequence of characters as the context vector 412 as a plurality of values and/or indices corresponding to respective ones input characters. In one embodiment, in order to derive the vectors, each character is assigned a value or position. For example, if 58 characters are recognized (e.g., associating to letters A-Z, capital letters A-Z, and numbers 0-9) a 1×58 vector is created for each character. In this instance, the vector for the character "a" would be comprised of a 1 at the first position, and 0's for all remaining positions.

The decoder 404 is configured to receive the context vector 412 from the encoder 402 and to generate a prediction vector 416 which is run through a softmax function 418 after each time step. The resulting prediction vector 416 comprises probabilities for each character in model's character vocabulary at each time step, i.e. for each location of the maximum output string length. In one embodiment, an output string 420 is formed by taking the most probable character at each time step prior to an EOS character. In some embodiments, a plurality of most likely output strings are formed using the prediction vector 416. In some embodiments, a beam search is used at each time step to determine the N best candidates, as opposed to simply choosing the most likely character at each time step.

In addition to the output string 420, a confidence factor 422 is also determined. The confidence factor 420 is a number between zero and one that indicates a confidence that the output string 420 is correct. The confidence factor 420 is calculated based probability of each selected character of the output string 420, as indicated by the prediction vector 416. Particularly, in at least one embodiment, the confidence factor 420 is calculated by multiplying probability of each selected character of the output string 420. In some embodiments, a confidence threshold is used to determine whether a spelling correction should be performed. Particularly, in one embodiment, the spelling correction model 230 only performs a spelling correction if the confidence factor 422 for the output string 420 is greater than a confidence threshold (e.g., 0.9).

As discussed above, the spelling correction model 230 is trained using text fields of the consumable records 224. Particularly, in some embodiments, the model is trained using a description field of each consumable record 224, which includes a text string that identifies and/or describes the consumable item. Similarly, in some embodiments, the model may also be trained using an ingredients field of each consumable record 224, which includes a text string that identifies and/or describes the ingredients for the consumable item. As used herein, the term "train" refers to providing pairs of exemplary encoder inputs and decoder outputs to a machine learning model and identifying patterns and statistical relationships or structures in the data such that the machine learning model can predict an output given new inputs.

Before training the model, the consumable records 224 are filtered to identify a training subset of the consumable records 224 having correct spelling. The text fields from the training subset are used as the ground truth for the purposes of training the model. Accordingly, it is important for the text fields from the training subset to be as error-free as possible. In some embodiments, only the most frequently logged consumable records 224 are included in the training subset, based on an assumption that these records are very likely to have correct spelling. In this case, it is assumed that correct spellings will be recognized and selected by users more often than incorrect spellings (e.g., "pear" will be selected for commonly than "pair"). Similarly, in some embodiments, only consumable records 224 created by users located in English-speaking countries and/or users having their language settings set to English. In this case, it is assumed that users who have selected English in their language settings or are located in English-speaking countries are more familiar with English spellings. Other languages would be used to filter the consumables records when training the model for spelling in another language.

Once a set of training data having correct spelling has been generated, input data is artificially generated having incorrect spelling. Particularly, for each string in the set of training data having correct spelling, a plurality of incorrect spellings are artificially generated by systematically introducing errors into the string having correct spelling, e.g. by randomly swapping characters, adding characters, deleting characters, moving spaces, adding spaces, deleting spaces, etc. The artificially generated strings having incorrect spelling are paired with the strings having correct spelling and labeled as input and output data, respectively. Some exemplary string pairs may include [input: "ic ecream", output: "ice cream"]; [input: "ice creeem", output: "ice cream"]; and [input: "ece cram", output: "ice cream"].

The pairs of incorrectly and correctly spelled strings are fed into the model 400 in batches. In the batch processing, each of the strings are preprocessed as discussed above. The characters are encoded, yielding a tensor for each batch with dimensions equal to the number of examples per batch, the maximum allowed input length, and the number of characters in the character vocabulary. In one embodiment, the model is trained using categorical cross-entropy with an Adam optimizer with a patience of 5 epochs, after which if validation loss does not increase, training terminates. In one embodiment, a batch size of 100 is used with a number of steps per epoch equal to the number of examples divided by the batch size. In this way, all examples are seen in each epoch. The ordering of the training examples is shuffled between each epoch. In one embodiment, the new sets of strings having incorrect spelling are randomly generated, as discussed above, between each epoch.

After training, the spelling correction model 230 can be used by the health tracking system 100 to perform spelling correction and to implement various useful features for the health tracking system 100. Unlike traditional spelling correction models, the spelling correction model 230 provides context-sensitive spelling correction because the model considers the words around a misspelled word. For example, given the incorrectly spelled string "lemon merang pie," a traditional spelling correction solution might output the string "lemon merengue pie." However, the spelling correction model 230 is more likely to output "lemon meringue pie" because the word "meringue" is more likely correct than the word "merengue" based on the surrounding words "lemon" and "pie". Additionally, because the model is trained using a narrow set of food related training data, it is positively biased towards food related spelling corrections giving it better domain-sensitivity than a traditional spelling correction model. For example, given the incorrectly spelled string "low tat milk," a traditional spelling correction solution might output the string "low tar milk." However, the spelling correction model 230 is more likely to output "low fat milk" because the word "fat" is likely common in the training data and the word "tar" may not even exist in the training data. In some embodiments, multiple instances of the spelling correction model 230 can be used for different purposes, e.g. a first instance for correcting spelling in consumable item description text fields and a second instance for correcting spelling in ingredient text fields. In this way, there is stronger domain-sensitivity for each usage of the model.

Methods for operating the health tracking system 100 are described below. In particular, methods for operating the health tracking system 100 to train and use the spelling correction model 230 are discussed below. In the description of the methods, statements that a method is performing some task or function refers to a controller or general purpose processor executing programmed instructions stored in non-transitory computer readable storage media operatively connected to the controller or processor to manipulate data or to operate one or more components in the health tracking system 100 to perform the task or function. Particularly, the processor circuitry/logic 204 of the system server 200 and/or the processor 308 of the smartphone 110A above may be such a controller or processor. Alternatively, the controller may be implemented with more than one processor and associated circuitry and components, each of which is configured to form one or more tasks or functions described herein. Additionally, the steps of the methods may be performed in any feasible chronological order, regardless of the order shown in the figures or the order in which the steps are described.

The herein described applications and methods utilizing the spelling correction model 230 (e.g., the health tracking program 218 and/or health tracking application 316) improve the functioning of the processing circuitry/logic 204 and/or the processor 308, respectively or in combination by enabling it/them to perform domain and context sensitive spelling correction. Furthermore, devices that are able to perform domain and context sensitive spelling correction can operate more efficiently to maintain and search the consumable records database 224.

Method of Training the Spelling Correction Model

FIG. 5 shows a method 500 of operating the health tracking system 100 to train the spelling correction model 100. The method 500 begins with a step of storing a plurality of data records, each of the plurality of data records comprising at least a descriptive string and nutritional data regarding a respective consumable item (block 510). Particularly, as discussed above, the processing circuitry/logic 204 of the server 200 is configured to maintain a consumable records database 224 in the memory 206. Each consumable record 224 includes one or more text strings related to a consumable item, such as an item description or an ingredient list, as well as nutritional information.

The method 500 continues with a step of filtering the plurality of data records to identify a subset thereof, the subset comprising those records in which the respective descriptive strings have correct spellings of every word contained therein (block 520). Particularly, the processing circuitry/logic 204 of the server 200 is configured to filter the consumable records 224 to identify a subset of the consumable records 224 in which the text fields have correct spelling. The identified subset of the consumable records 224 are be used as the ground truth, i.e. exemplary correct outputs, for training the spelling correction model 230. In one embodiment, the processing circuitry/logic 204 is configured to determine a frequency with which each consumable record 224 is selected by users to be logged in his or her food diary and identify the subset of the consumable records 224 as those which are logged most frequently by users. In one embodiment, the processing circuitry/logic 204 is configured to determine a language setting of the users who originally created each consumable record 224 and identify the subset of the consumable records 224 on the basis of the language setting of the users who originally created each consumable record 224. Particularly, in one embodiment, only consumable records created by users having English language setting are included in the subset of consumable records used for training. In one embodiment, the processing circuitry/logic 204 is configured to determine a location setting of the users who originally created each consumable record 224 and identify the subset of the consumable records 224 on the basis of the location setting of the users who originally created each consumable record 224. Particularly, in one embodiment, only consumable records created by users having an English speaking country (e.g., the United States of America) selected as their location are included in the subset of consumable records used for training. Similar filtering may be used to train the spelling correction model 230 for additionally languages.

The method 500 continues with a step of generating, for each data record in the identified subset of the plurality of data records, a plurality of companion descriptive strings, each of the companion descriptive strings comprising an incorrect spelling of at least one word contained therein (block 530). Particularly, the processing circuitry/logic 204 of the server 200 is configured to generate a plurality of incorrectly spelled text strings for each correctly spelled text string by introducing errors into the string having the correct spelling, e.g. by randomly swapping characters, adding characters, deleting characters, moving spaces, adding spaces, deleting spaces, etc. In one embodiment, the processing circuitry/logic 204 of the server 200 is configured to generate a predetermined number (e.g., 10) of incorrectly spelling text strings for each of the correctly spelled text strings. The processing circuitry/logic 204 of the server 200 is configured to pair the each of the incorrectly spelled text strings with the respective correctly spelled text strings for training of the spelling correction model 230.

The method 500 continues with a step of training a machine learning model using pairs of descriptive strings, each pair of descriptive strings including (i) the descriptive string of a respective data record in the identified subset of the plurality of data records, and (ii) a corresponding one of the companion descriptive strings having at least one word thereof incorrectly spelled (block 540). Particularly, the processing circuitry/logic 204 of the server 200 is configured to feed the pairs of incorrectly spelled and correctly spelled strings to the spelling correction model 230. More particularly, during a training process of the spelling correction model 230, the processing circuitry/logic 204 provides the incorrectly spelled strings to the spelling correction model 230 as example inputs and the corresponding correctly spelled strings to the spelling correction model 230 as example outputs. In one embodiment, the processing circuitry/logic 204 is configured to preprocess text strings and train the model 230 in using batches of example text string pairs, as discussed in more detail above.

Method of Correcting Records in Consumable Records Database

Figure 6:
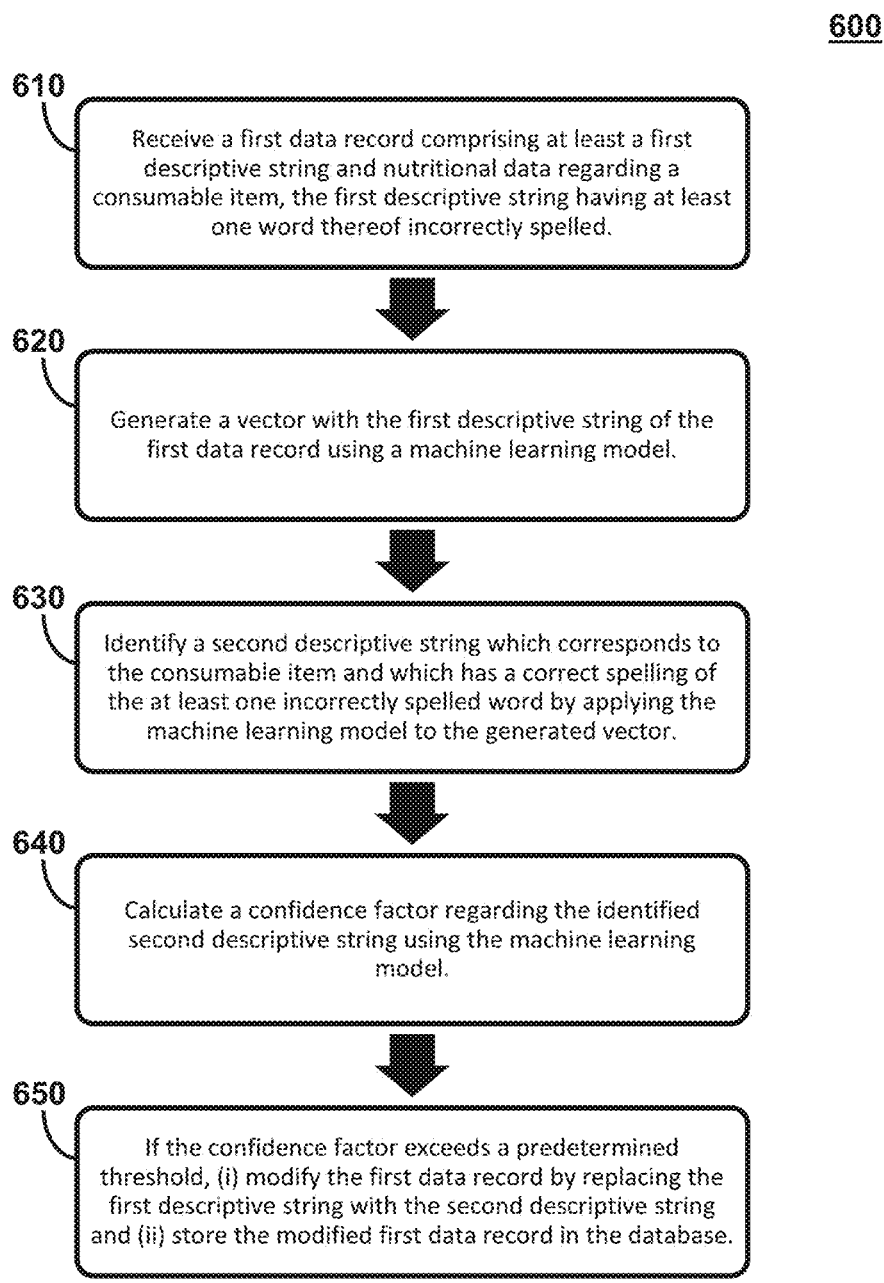
FIG. 6 shows a method of operating the health tracking system to correct spelling in consumable records using the spelling correction model.

FIG. 6 shows a method 600 of operating the health tracking system 100 to correct spelling in consumable records using the spelling correction model 230. The method 600 begins with a step of receiving a first data record comprising at least a first descriptive string and nutritional data regarding a consumable item, the first descriptive string having at least one word thereof incorrectly spelled (block 610). Particularly, the processing circuitry/logic 204 of the server 200 is configured to receive a consumable record having nutritional information and at least one text string regarding a consumable item. In some instances, the received consumable record is a newly created consumable record received from a health tracking device 110 of a user that created the consumable record. In other instances, the received consumable record is an existing consumable record stored in the consumable record database 224. In this way, the method 500 can be utilized to correct spelling in newly created consumable records, as well as to correct spelling in existing consumable records stored in the consumable record database 224.

The method 600 continues with a step of generating a vector with the first descriptive string of the first data record using a machine learning model (block 620). Particularly, the processing circuitry/logic 204 of the server 200 is configured to extract a text string from the consumable record and to generate a context vector based on the sequence of characters that comprise the text string using the spelling correction model 230. More particularly, the processing circuitry/logic 204 is configured to encode the context vector using the encoder 402 of the spelling correction model 230 as a plurality of values corresponding to respective ones of a sequence of characters that comprises the text string, as described in more detail above. In one embodiment, the processing circuitry/logic 204 is configured to preprocess the text string prior to encoding the context vector, as discussed in more detail above.

The method 600 continues with a step of identifying a second descriptive string which corresponds to the consumable item and which has a correct spelling of the at least one incorrectly spelled word by applying the machine learning model to the generated vector (block 630). Particularly, the processing circuitry/logic 204 of the server 200 is configured to generate a correctly spelled text string based on the context vector using the spelling correction model 230. More particularly, the processing circuitry/logic 204 is configured to determine a prediction vector based on the context vector using the decoder 404 of the spelling correction model 230 and generate a correctly spelled text string based on the prediction vector by taking the most probably character at each time step, as discussed in greater detail above.

The method 600 continues with a step of calculating a confidence factor regarding the identified second descriptive string using the machine learning model (block 640). Particularly, the processing circuitry/logic 204 of the server 200 is configured to calculate a confidence factor regarding the generated correctly spelled text string using the spelling correction model 230. More particularly, the processing circuitry/logic 204 is configured to calculate the confidence factor based on the probability, as indicated by the prediction vector, of each character of the generated correctly spelled text string, as discussed in greater detail above.

If the confidence factor exceeds a predetermined threshold, the method 600 continues with the steps of modifying the first data record by replacing the first descriptive string with the second descriptive string and storing the modified first data record in the database (block 650). Particularly, in response to the confidence factor exceeding a predetermined threshold (e.g. 0.9 or 90%), the processing circuitry/logic 204 of the server 200 is configured to replace the text string of the received consumable record with the generated correctly spelled text string and to store the corrected consumable record in the consumable records databases 224. The threshold value may be selected by a network operator in one example. In response to the confidence factor being below the predetermined threshold, the processing circuitry/logic 204 is configured to store the received consumable record in the consumable records databases 224 without modification.

Similar logic may be used to enable real-time corrections to a user entered consumable item (including e.g., recipes). That is, when a user creates a new record, the aforementioned spelling corrector may be applied to ensure that each word thereof is correctly spelled.

Method of Searching the Consumable Records Database

Figure 7:
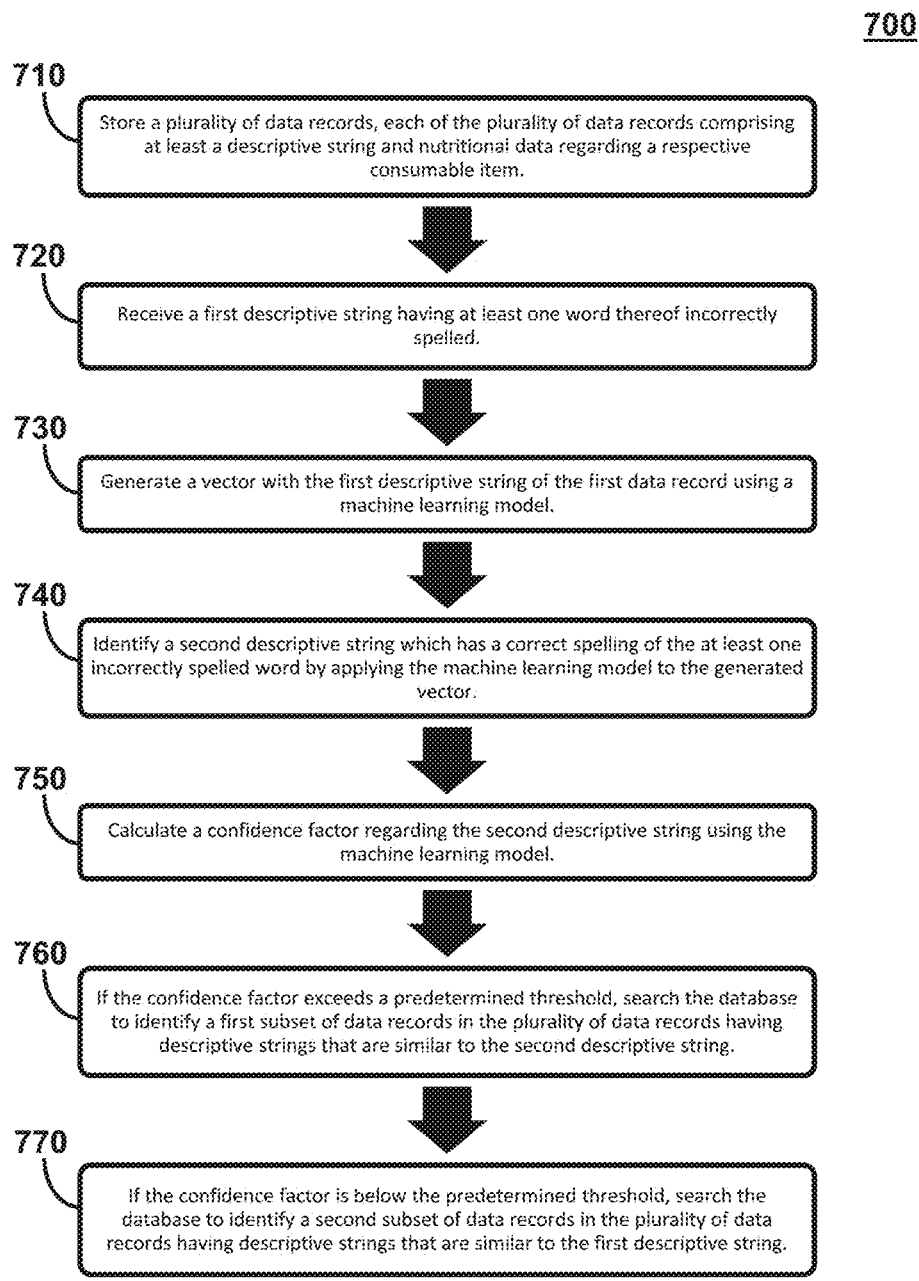
FIG. 7 shows a method of operating the health tracking system to provide improved consumable record search results using the spelling correction model.

FIG. 7 shows a method 700 of operating the health tracking system 100 to provide improved consumable record search results using the spelling correction model 230. The method 700 begins with a step of storing a plurality of data records, each of the plurality of data records comprising at least a descriptive string and nutritional data regarding a respective consumable item (710). Particularly, as discussed above, the processing circuitry/logic 204 of the server 200 is configured to maintain a consumable records database 224 in the memory 206. Each consumable record 224 includes one or more text strings related to a consumable item, such as an item description or an ingredient list, as well as nutritional information.

The method 700 continues with a step of receiving a first descriptive string having at least one word thereof incorrectly spelled (block 720). Particularly, the processing circuitry/logic 204 of the server 200 is configured to receive, from a health tracking device 110, a search string having an incorrectly spelled word. The search string may be, for example, a string entered by a user via a search window of a graphical user interface of the health tracking device 110. The search string is text string with which the user would like to search the consumable records database 224 so that he or she may select consumable records to be logged in his or her food diary.

The method 700 continues with a step of generating a vector with the first descriptive string of the first data record using a machine learning model (block 730). Particularly, the processing circuitry/logic 204 of the server 200 is configured to generate a context vector based on the sequence of characters that comprise the search string using the spelling correction model 230. More particularly, the processing circuitry/logic 204 is configured to encode the context vector using the encoder 402 of the spelling correction model 230 as a plurality of values corresponding to respective ones of a sequence of characters that comprises the search string, as described in more detail above. In one embodiment, the processing circuitry/logic 204 is configured to preprocess the search string prior to encoding the context vector, as discussed in more detail above.

The method 700 continues with a step of identifying a second descriptive string which has a correct spelling of the at least one incorrectly spelled word by applying the machine learning model to the generated vector (block 740). Particularly, the processing circuitry/logic 204 of the server 200 is configured to generate a correctly spelled search string based on the context vector using the spelling correction model 230. More particularly, the processing circuitry/logic 204 is configured to determine a prediction vector based on the context vector using the decoder 404 of the spelling correction model 230 and generate a correctly spelled search string based on the prediction vector by taking the most probably character at each time step, as discussed in greater detail above.

The method 700 continues with a step of calculating a confidence factor regarding the second descriptive string using the machine learning model (block 750). Particularly, the processing circuitry/logic 204 of the server 200 is configured to calculate a confidence factor regarding the generated correctly spelled search string using the spelling correction model 230. More particularly, the processing circuitry/logic 204 is configured to calculate the confidence factor based on the probability, as indicated by the prediction vector, of each character of the generated correctly spelled search string, as discussed in greater detail above.

Figure 8:
FIG. 8 shows a graphical user interface showing improved search results.

If the confidence factor exceeds a predetermined threshold, the method 700 continues with a step of searching the database to identify a first subset of data records in the plurality of data records having descriptive strings that are similar to the second descriptive string (block 760). Particularly, in response to the confidence factor exceeding a predetermined threshold (e.g. 0.9 or 90%), the processing circuitry/logic 204 of the server 200 is configured to search the consumable records database 224 for consumable records having an item description or ingredient description that is similar to the generated correctly spelled search string. In this way, the search of the consumable records database 224 is performed using the corrected search string only if the spelling correction model 230 is sufficiently confident in its spelling correction. In one embodiment, the processing circuitry/logic 204 is configured to transmit the search results to the health tracking device 110 so that the user can view and select from the search results which items he or she would like to log in his or her food diary. The search results may be displayed on the screen of the health tracking device 110A, as shown in the exemplary graphical user interface of FIG. 8. Particularly, FIG. 8 shows an incorrectly spelled search string "Low yat yogurt" in a search window 810 of a graphical user interface. However, the spelling correction model 230 predicted with a confidence factor greater than 0.9 that the user meant to type "Low fat yogurt." Accordingly, search results 820 are provided on the basis of the corrected search string. As can be seen the search results advantageously include consumable records relating to "Low fat yogurt," which the user likely meant to type.

Figure 9:
FIG. 9 shows a graphical user interface showing search results.

If the confidence factor is below the predetermined threshold, the method 700 continues with a step of searching the database to identify a second subset of data records in the plurality of data records having descriptive strings that are similar to the first descriptive string (block 770). Particularly, in response to the confidence factor being below the predetermined threshold, the processing circuitry/logic 204 of the server 200 is configured to search the consumable records database 224 for consumable records having an item description or ingredient description that is similar to the received search string (rather than the corrected search string). In this way, the search of the consumable records database 224 is performed using the search string "as is" only if the spelling correction model 230 is sufficiently confident in its spelling correction. As above, the processing circuitry/logic 204 is configured to transmit the search results to the health tracking device 110 so that the user can view and select from the search results which items he or she would like to log in his or her food diary. The search results may be displayed on the screen of the health tracking device 110A, as shown in the exemplary graphical user interface of FIG. 9. Particularly, FIG. 9 shows an incorrectly spelled search string "Cie creeem" in a search window 910 of a graphical user interface. The spelling correction model 230 may have predicted that the user meant to type "Ice cream," but the confidence factor was less than 0.9. Accordingly, search results 920 are provided on the basis of the original incorrectly spelled search string.

It will be appreciated that the various ones of the foregoing aspects of the present disclosure, or any parts or functions thereof, may be implemented using hardware, software, firmware, tangible, and non-transitory computer readable or computer usable storage media having instructions stored thereon, or a combination thereof, and may be implemented in one or more computer systems.

Particularly, in some embodiments, a permanent copy of the programming instructions for individual ones of the aforementioned applications utilizing the spelling correction model 230 (e.g., the health tracking program 218 and/or health tracking application 316) may be placed into permanent storage devices (such as e.g., the memory 206 and/or the memory 310) during manufacture thereof, or in the field, through e.g., a distribution medium (not shown), such as a compact disc (CD), or through communication interface 212, 304 from a distribution server (such as the server 200 and/or another distribution server). That is, one or more distribution media having an implementation of the agent program may be employed to distribute the agent and program various computing devices.

The foregoing detailed description of one or more exemplary embodiments of the health tracking system 100 has been presented herein by way of example only and not limitation. It will be recognized that there are advantages to certain individual features and functions described herein that may be obtained without incorporating other features and functions described herein. Moreover, it will be recognized that various alternatives, modifications, variations, or improvements of the above-disclosed exemplary embodiments and other features and functions, or alternatives thereof, may be desirably combined into many other different embodiments, systems or applications. Presently unforeseen or unanticipated alternatives, modifications, variations, or improvements therein may be subsequently made by those skilled in the art which are also intended to be encompassed by the appended claims. Therefore, the spirit and scope of any appended claims should not be limited to the description of the exemplary embodiments contained herein.

What is claimed is:

1. A method of operating a health tracking system, the method comprising:
   receiving a first data record comprising at least a first descriptive string and nutritional data regarding a consumable item, the first descriptive string having at least one word thereof having a first character sequence;
   generating a data storage element with the first descriptive string of the first data record using a machine learning model;
   identifying a second descriptive string which corresponds to the consumable item and which has a second character sequence for the at least one word by applying the machine learning model to the generated data storage element;
   calculating a confidence factor regarding the identified second descriptive string using the machine learning model; and
   when it is determined that the confidence factor exceeds a predetermined threshold:
      modifying the first data record by replacing the first descriptive string with the second descriptive string; and
      storing the modified first data record in a database.

2. The method according to claim 1, wherein the act of generating the data storage element comprises generating a vector including:
   generating a plurality of values corresponding to respective ones of a sequence of characters that comprises the at least one word of the first descriptive string; and
   forming the vector using the generated plurality of values.

3. The method according to claim 1, wherein the first character sequence is an incorrect spelling of the at least one word and the second character sequence is a correct spelling of the at least one word wherein the act of identifying the second descriptive string comprises:
   determining, for each character of a sequence of characters that comprises the second descriptive string, a most probable correct character by applying the machine learning model to the generated data storage element; and
   forming the second descriptive string using the determined most probable correct characters.

4. The method according to claim 3, wherein the act of calculating the confidence factor comprises:
   calculating the confidence factor based on probabilities of the determined most probable correct characters.

5. The method according to claim 1, further comprising:
   storing a plurality of data records in the database, each of the plurality of data records comprising at least a descriptive string and nutritional data regarding a consumable item;
   identifying a subset of the plurality of data records; and
   training the machine learning model using the identified subset of the plurality of data records.

6. The method according to claim 5, wherein the first character sequence is an incorrect spelling of the at least one word and the second character sequence is a correct spelling of the at least one word wherein the act of identifying the subset of the plurality of data records comprises:
   filtering the plurality of data records to identify data records in the plurality of data records in which the respective descriptive strings have correct spellings of every word contained therein.

7. The method according to claim 5, wherein the act of training the machine learning model comprises:
   generating, for each data record in the identified subset of the plurality of data records, a plurality of companion descriptive strings having at least one word thereof incorrectly spelled;
   training the machine learning model using pairs of descriptive strings, each pair of descriptive strings including (i) the descriptive string of a respective data record in the identified subset of the plurality of data records and (ii) a corresponding one of the companion descriptive strings having at least one word thereof incorrectly spelled.

8. The method according to claim 7, wherein the act of generating the plurality of companion descriptive strings comprises:
   introducing one or more spelling errors into the descriptive strings of the identified subset of the plurality of data records.

9. The method according to claim 1, wherein the machine learning model includes an encoder having at least one long short term memory layer and a decoder having at least one long short term memory layer.

10. The method according to claim 1, further comprising:
prior to generating the data storage element, appending padding characters to the first descriptive string such that the first descriptive string has predetermined character length.

11. A method of operating a health tracking system having a database configured to store a plurality of data records, each of the plurality of data records comprising at least a descriptive string and nutritional data regarding a respective consumable item, the method comprising:
receiving a first data record comprising at least a first descriptive string and nutritional data regarding a first consumable items, the first descriptive string having at least one word thereof spelled with a first spelling;
generating a data storage element with the first descriptive string using a machine learning model;
identifying a second descriptive string which corresponds to the first consumable item and has a second spelling of the at least one word by applying the machine learning model to the generated data storage element;
calculating a confidence factor regarding the second descriptive string using the machine learning model;
when it is determined that the confidence factor exceeds a predetermined threshold, searching the database to identify a first subset of data records in the plurality of data records having descriptive strings that are similar to the second descriptive string; and
when it is determined that the confidence factor is below the predetermined threshold, searching the database to identify a second subset of data records in the plurality of data records having descriptive strings that are similar to the first descriptive string.

12. The method according to claim 11, wherein the act of generating the data storage element comprises:
generating a plurality of values corresponding to respective ones of a sequence of characters that comprises the at least one word of the first descriptive string; and
forming a vector using the generated plurality of values.

13. The method according to claim 11, wherein the act of identifying the second descriptive string comprises:
determining, for each character of a sequence of characters that comprises the second descriptive string, a most probable correct character by applying the machine learning model to the generated data storage element; and
forming the second descriptive string using the determined most probable correct characters.

14. The method according to claim 13, wherein the act of calculating the confidence factor comprises:
calculating the confidence factor based on probabilities of the determined most probable correct characters.

* * * * *